(12) United States Patent
Schaerer et al.

(10) Patent No.: US 8,988,505 B2
(45) Date of Patent: Mar. 24, 2015

(54) IMAGING SYSTEM USING MARKERS

(75) Inventors: Shawn Schaerer, Winnipeg (CA); Gordon Scarth, Winnipeg (CA); Steven Robbins, Winnipeg (CA)

(73) Assignee: Imris Inc, Winnipeg, MB (CA)

( * ) Notice: Subject to any disclaimer, the term of this patent is extended or adjusted under 35 U.S.C. 154(b) by 605 days.

(21) Appl. No.: 12/907,398

(22) Filed: Oct. 19, 2010

(65) Prior Publication Data

US 2011/0254922 A1    Oct. 20, 2011

Related U.S. Application Data (60) Provisional application No. 61/253,330, filed on Oct. 20, 2009.

(51) Int. Cl.
 *H04N 13/02* (2006.01)
 *A61B 19/00* (2006.01)

(52) U.S. Cl.
 CPC ............. *A61B 19/5244* (2013.01); *A61B 19/44* (2013.01); *A61B 2019/444* (2013.01); *A61B 2019/5255* (2013.01); *A61B 2019/5265* (2013.01); *A61B 2019/5483* (2013.01)
 USPC .......................................................... 348/46

(58) Field of Classification Search
 CPC ............... A61B 19/44; A61B 19/5244; A61B 2019/444; A61B 2019/5255; A61B 2019/5265; A61B 2019/5483; H04N 13/0239
 USPC ........................................... 348/46; 600/426
 See application file for complete search history.

(56) References Cited

U.S. PATENT DOCUMENTS

| | | |
|---|---|---|
| 5,662,111 A | 9/1997 | Cosman |
| 5,828,770 A | 10/1998 | Leis |
| 5,923,417 A | 7/1999 | Leis |
| 6,006,126 A | 12/1999 | Cosman |
| 6,026,315 A | 2/2000 | Lenz |
| 6,161,033 A * | 12/2000 | Kuhn ............................ 600/429 |
| 6,175,610 B1 * | 1/2001 | Peter ................................ 378/8 |
| 6,351,661 B1 | 2/2002 | Cosman |
| 6,381,485 B1 | 4/2002 | Hunter |
| 6,405,072 B1 | 6/2002 | Cosman |
| 6,490,473 B1 | 12/2002 | Katznelson |
| 6,516,213 B1 | 2/2003 | Nevo |
| 6,556,722 B1 * | 4/2003 | Russell et al. ................ 382/291 |
| 6,584,174 B2 | 6/2003 | Schubert |
| 6,609,022 B2 | 8/2003 | Vismeier |
| 6,714,629 B2 | 3/2004 | Vismeier |

(Continued)

FOREIGN PATENT DOCUMENTS

WO    2006065563    6/2006

*Primary Examiner* — Anner Holder
(74) *Attorney, Agent, or Firm* — Adrian D. Battison; Ade & Company Inc (57) ABSTRACT

A system for detecting a position of an object such as a surgical tool in an image guidance system includes a camera system with a detection array for detecting visible light a processor arranged to analyze the output from the array. Each object to be detected carries a single marker with a pattern of contrasted areas of light and dark intersecting at a specific single feature point thereon. The pattern includes components arranged in an array around the specific location arranged such that the processor is able to detect an angle of rotation of the pattern around the location and which are different from other markers of the system such that the processor is able to distinguish each marker from the other markers.

16 Claims, 4 Drawing Sheets

(56) References Cited

U.S. PATENT DOCUMENTS

| | | |
|---|---|---|
| 6,871,086 B2 | 3/2005 | Nevo |
| 6,978,167 B2 | 12/2005 | Dekel |
| 7,111,423 B2 | 9/2006 | Lizotte et al. |
| 2009/0171196 A1 | 7/2009 | Olson |
| 2010/0168562 A1* | 7/2010 | Zhao et al. .................... 600/426 |

* cited by examiner

IMAGING SYSTEM USING MARKERS

This application claims the benefit of Priority under 35 USC 119 from Provisional Application 61/253,330 filed Oct. 20, 2009.

This invention relates to an imaging system using markers with a camera responsive to visible light for detecting the markers. This system can be used for example for locating a position of an object in a field of view. The invention is particularly but not necessarily related to such detection systems for use in image guided surgery (IGS) where the object is a surgical tool.

This application is related to co-pending U.S. application Ser. No. 12/913,155 filed Oct. 27, 2010 which claims priority from Provisional Application 61/255,735 filed Oct. 28, 2009, the disclosure of which is incorporated herein by reference.

The image for the IGS can be obtained from any modality including MRI, CT, X-Ray, PET, Angio and Ultrasound.

The imaging system can be used in surgical systems or in non-surgical systems.

BACKGROUND OF THE INVENTION

An Image Guided Surgery System (IGS) provides a surgeon with spatial information. Typically, an IGS is used to indicate to the surgeon where the end or parts of a surgical tool is within or around the human body. For example, during brain surgery, one end of the tool might be in the surgeon's hand and the other end of the tool could be inside the patient, when it would not normally be visible. An IGS system finds the end of the tool that is outside the body, calculates (from tool geometry) where the other end of the tool is, and then registers the location of the tool with the prior images of the interior of the brain U.S. Pat. No. 6,978,167 (Dekel) issued Dec. 20, 2005 to Claron Technology Inc discloses a method for detecting and tracking the pose of an object such as a surgical tool displaceable in a coordinate reference frame. A visible target pattern on a marker includes a series of contrast regions of dark and light for providing feature points at which the dark and light regions meet at a juncture of an optically detectable plurality of edges. The method and system determine the location of the feature points by first locating the edges using the change in contrast between contrast regions, and then determining junctures of multiple edges. A stereoscopic digital camera generates a pair of digital images of the target pattern and a marker template comprising a set of reference characteristics including a relationship between the feature points.

This patent discloses in detail a method for detecting the feature point at the junction of the contrasting regions, which method is particularly applicable herein so that the details of this patent are hereby incorporated by reference or may be referred to for further detail of the method.

U.S. Pat. No. 5,828,770 (Leis) issued Oct. 27, 1998 to Northern Digital Inc discloses a system for determining the spatial position and angular orientation of an object in real-time is provided having a sensor section and a plurality of markers which emit a detectable energy. The markers are activated in an initial marker-identification mode. With such system, because the markers have been each uniquely identified during the marker-identification mode, and the relative marker geometry is known, the markers are simultaneously activated, detected and tracked during a subsequent marker-tracking mode.

U.S. Pat. No. 5,923,417 (Leis) issued Jul. 13, 1999 to Northern Digital Inc discloses a similar system which includes a common energy detector for detecting both the energy emitted by an active target and the energy reflected by a passive target.

Existing state-of-the-art tracking technologies claims to have accuracy in the 2 mm range. These devices typically use infra-red or other non-visible optical tracking technology and suffer from a number of limitations including reduced capabilities with angulations of the tracked tool, difficulties in positioning a reference frame for tracking, inaccuracies from the positioning of the tracking reference as compared with the tracking field of view, and inaccuracies causes be contaminants (e.g., fingerprint on IR tracking sphere). These common problems lead to poor utility and inaccuracies in tracking tools during surgery.

Relying on multiple markers can increase the system error (larger inaccuracy), increase the footprint/size of the tracked device and lead to poor ergonomic design of tracked devices. The use of multiple generic markers in motion tracking applications (respiratory motion tracking) can place motion constraints on the tracking system that can lead to inaccuracies in motion tracking.

The standard markers that are available on the market today (IR spheres, X Points) do not have sufficient information associated with each marker to allow the use of a single marker (one IR sphere or X Point) to be used for tracking an object/device. This information only allows for a tracking system to measure the translational information of a single marker, since the system cannot determine rotational information from a sphere or symmetrical pattern. Tracking systems also have a problem distinguishing one marker from another, so the inclusion of multiple generic markers in a tracking systems field of view creates the problem of uniquely determining the identity of each marker and the object associated with it. If the objects are at rest the system could determine which object is associated with each marker, but if the objects are moving then the system will have a difficult time distinguishing one marker from another.

In order for these markers to be used in a tracking system multiple markers must be used and configured in a unique geometric pattern. Each unique pattern and associated markers are affixed to an object that needs to be tracked. This allows the tracking system to identify and track objects using multiple markers. Using multiple markers to construct a pattern has several disadvantages. The first disadvantage is that the size of the pattern will increase the footprint of the tracked object which could affect its usefulness. The second disadvantage is that since there is a large marker pattern associated with a tracked device, the ergonomic design of the device will be impacted. The final disadvantage is that the accuracy of detecting the position and orientation of a tracked object can be degraded. The accuracy of a tracked object is related to the accuracy in detecting the markers that are associated with it and the geometry of the pattern. Each marker has an associated error and when multiple markers are used this error can be compounded and magnified by the pattern's geometry.

SUMMARY OF THE INVENTION

It is one object of the invention to provide an imaging system which provides visual encoding of the markers.

According to a first aspect of the invention there is provided a imaging system comprising:

a plurality of markers;

a camera system for detecting visible light including at least one camera with a detector array for detecting light in a field of view and providing an output responsive thereto;

a processor arranged to analyze the output;

wherein each of the marker includes a pattern thereon which is detectable by the detector array to be analyzed by the processor;

wherein the pattern includes first components arranged such that the processor is able to detect a specific location in three dimensions on the marker; and wherein the pattern on each of the markers includes second components different from other markers of the system arranged to provide an encoding such that the processor is able to distinguish each marker from the other markers.

There are many techniques and methods to visually encode the marker.

1. A simple solution is to use a series of different sized curved line segments around a checkerboard marker (see picture Example Marker Complex Patterns). Based on the length and number of the line segments, the marker is encoded. To obtain rotational information of a circular marker one point on the ring containing the line segments will be labelled to be the origin of the marker. To enhance the rotational information of a marker, the marker can be elongated with the thinnest point of the elongated side being designated as the origin (Example Marker Complex Patterns—Isometric View or Ellipsoidal).

2. Another technique to visually encode a marker would be to surround the marker with a small unobtrusive 2D bar code. The bar code would contain the marker ID and the shape of the marker would provide rotational information.

3. Markers can also be encoded in 3D by using small protrusions or indentations in the marker, or areas of the markers which are raised or recessed relative to other areas. These 3D features give the flexibility to use the same marker pattern with the marker ID being provided by these raised or recessed features.

4. The encoding techniques provided have only been for black and white markers. Markers can also be encoded using colour information (see Example Marker Complex Patterns—Colors). Colour information adds another dimension to marker encoding.

Visually encoded markers can be used in any camera technology and the camera can be monochromatic, full colour or any one of the single colour channels (red, green or blue).

They also can be used in different light conditions by means of using passive (e.g. phosphorescence) or active (e.g. LED light) illumination. The illumination increases the likelihood that the marker will be identified in sub-optimal lighting condition.

These markers are not limited to just surgical tools; they can be applied to other surgical and non-surgical equipment such as booms, MRI, C-Arms and lights. The markers can also be utilized in surgical robotic systems where knowing the precise location of the end effector is critical and where end effector real estate is limited.

Visual encoding an optical marker allows a system to track objects or targets with the use of a single marker. Current systems rely on multiple markers arranged in geometrical patterns to track objects. A single marker leads to a smaller footprint for tracking (as it does not need a large geometrical pattern) and can improve overall accuracy of the system. Accuracy is affected by image noise and every marker has an error associated with it due to this noise. Error is compounded when multiple markers are used and this error can be magnified when multiple markers are arranged in a geometrical pattern. Therefore use of a single marker can improve system accuracy by reducing the effects of image noise.

An encoded marker also makes it easier for a system to identify the position and orientation of a marker. Given an application on respiratory motion tracking where there are dozens of markers placed on a patient's abdomen, it is difficult for the system to automatically identify and track markers with the same pattern. In order for the system to track these markers, marker movement is constrained to a small value per update.

Using encoded markers removes this constraint since this system can identify and track each unique marker at any given time, no matter how far they have moved.

The arrangement herein can be used in a surgical tracking system that addresses common deficiencies leading to a better workflow and higher average accuracy. The system includes an optical tracking system tailored to surgical tracking of devices consisting of one or more optical cameras, one or more optical references containing optical markers, devices to track containing different optical markers, and a computer processing capability to perform the tracking calculations and to display the results. Devices to be tracked include but are not limited to medical tools (e.g. probes), medical devices (e.g. microscopes, catheters, etc.), and other devices (booms, lights, carts, etc.). Patient position and motion can also be tracked.

Optical tracking allows the use of flat tracking markers (e.g. instead of spheres for IR) that contain patterns that can be identified optically. To successfully identify these markers, a pattern must be successfully identified. This includes a criterion for detecting the pattern. This is intrinsically more robust than technologies that identify a centroid of a mass (e.g. infra-red), since the criterion for identifying a shape such as a sphere is inherently less discriminatory than identifying a complex pattern. Also, fluids contaminating the tracking markers (e.g. from a fingerprint) that can adversely affect other tracking technologies (e.g. infra-red) even when they are not visible, do not have the same negative effect on optical markers because of the marker pattern identification criterion that must be satisfied. Thus, the optical markers can be designed to be more robust to contaminating fluids present during a surgery.

The marker patterns can also contain complex shapes, including combinations of squares (e.g. "checkerboard"), circles, rings and ellipsoids. They can also either be black and white, or include grey shades at different points in the pattern and/or other colors. They can also occur on faces of 3D shapes (e.g. cubes, etc). These complex patterns can advantageously be used to increase the robustness and overall accuracy of detection.

The tracking system based on optical markers can also be used to track patient motion. For example, by overlaying a pattern of flat optical markers on the chest of a patient, respiratory motion can be tracked in 3D. This can be used to trigger motion-correlating imaging (e.g., MR imaging) and also to correct for respiratory motion during post-processing of image data. Other patient motion can also be tracked, for example, hand or head movement.

Using flat tracking markers is intrinsically less obtrusive than markers extending from a tool so that they are visibly detectable (e.g. infra-red), and thus this can advantageously be used design a tool that is identifiable to the tracking system by using flat projections around the tool in two or more disjoint locations such that each set of such markers in a geometry adds to 180 degrees. Examples include 2 planes each 180 degrees apart, three planes each 60 degrees apart, four planes each 45 degrees apart, and so on. This allows the tool to be successfully tracked in any rotational orientation.

In a different orientation, round markers can be used instead of flat markers to give 360 degree of rotational coverage for any trackable object (e.g. the reference, tool, devices, etc.).

To aid the optical marker identification in different conditions, the patterns in the markers can be illuminated by active lighting (e.g. a light in behind the marker) and/or the markers can be enhanced to increase their likelihood of identification (e.g. phosphorescence). In addition, the optical marker patterns can be differentially enhanced within the marker pattern to further increase their detectability, and this can be applied differentially on separate markers that contain the same or different patterns.

To allow movement of one or more cameras, a tracking reference can be used. If the marker patterns are flat, then a tracking reference can contain a flat tracking pattern. However, since the object that the reference can be attached to for surgery (e.g. a head fixation device) can be placed in the surgical field at angles to optimize the effectiveness of the surgery independent of the effectiveness of the tracking system, the reference can be placed at angles that are sub-optimal for tracking. This can be address by an optical tracking reference that has several planes at different angles, with each plane containing either a unique or the same pattern that is identifiable by the optical tracking system. With this, the reference frame as an assembly could be mounted at sub-optimal angles, and by its design expose one or more optimal angles within the assembly to act as the optical tracking reference in that orientation. In addition, the so-described reference can be mounted in different optimal locations to further increase the optical reference accuracy (e.g. near the tracking field of view). The reference can also contain the tracking pattern on more than one side or plane of the reference, and this pattern can be the same or different from any other side or plane.

One or additional optical references can also be used advantageously to provide additional coverage of tracking with higher accuracy since the additional reference(s) can be placed at different angles and orientations to allow different optimal viewing angles from one or more cameras. In addition, since a single reference can be moved hampering the tracking performance, the additional references can be used to identify this movement and warm that tracking accuracy may be affected. Also, if or more references are used in total, then the relative locations of at least two of the references can then take over as the primary reference.

The arrangement described in more detail hereinafter may provide one or more of the following features and advantages:

- To provide a visual encoded marker for optical tracking systems that address the problems associated with the use of multiple generic markers.
- Visual encoded markers which solve the problems associated with tracking systems that use multiple generic markers. This allows a tracking system to easily identify each marker in the field of view, solving the problem of distinguishing one marker from another.
- Since each marker is now unique, each marker now has enough information associated with it that a tracking system can measure the translational and rotational position of each marker.
- Since the system can uniquely identify each marker, only one marker is needed per tracked object. This means that the overall footprint of the object can be reduced; the ergonomic design of the object can be improved and most importantly the overall accuracy of detecting an object's position is improved since the accuracy only depends on the error of detecting a single marker.
- A marker that is visually encoded contains a unique pattern and or shape that allows a tracking system to identify it.
- 360 degree rotational coverage of a tracking tool (system more likely to successfully track the probe in different orientations).
- Illumination of optical markers (active or passive) to allow their identification in different lighting conditions.
- Robustness of identification of the tracking markers for surgery due to the criterion to match a complex pattern rather than a simple geometric shape. Such markers are also allows more robust localization of the marker in the presence of fluids.
- Multiple references, each with different distinguishing configurations and locations to facilitate a better workflow and higher accuracy of tracking. This can include each reference having different angulations of markers to allow for different orientations of a head fixation device.
- Multiple cameras can be used optically to increase the accuracy from averaging the detection from each camera, and increase the effective field of view.
- Can be used to track patient motion (e.g. respiratory motion).
- Multiple cameras and multiple references can be used together to increase the accuracy.
- A single marker can be used instead of a many.
- A single encoded marker can provide spatial and rotational position. A single un-encoded marker cannot provide this because there is not enough information available.
- A single encoded marker can provide robustness of identification of the tracking markers for surgery due to the criterion to match a complex pattern rather than a simple geometric shape. Such markers are also allow more robust localization of the marker in the presence of fluids.
- Can take advantage of colour information, allowing for a larger number of unique markers to be generated.
- Can be used in surgical robotic systems to increase end effector accuracy.
- The system is robust to different lighting conditions.

BRIEF DESCRIPTION OF THE DRAWINGS

One embodiment of the invention will now be described in conjunction with the accompanying drawings in which.

In the drawing like characters of reference indicate corresponding parts in the figure.

DETAILED DESCRIPTION

Figure 1:
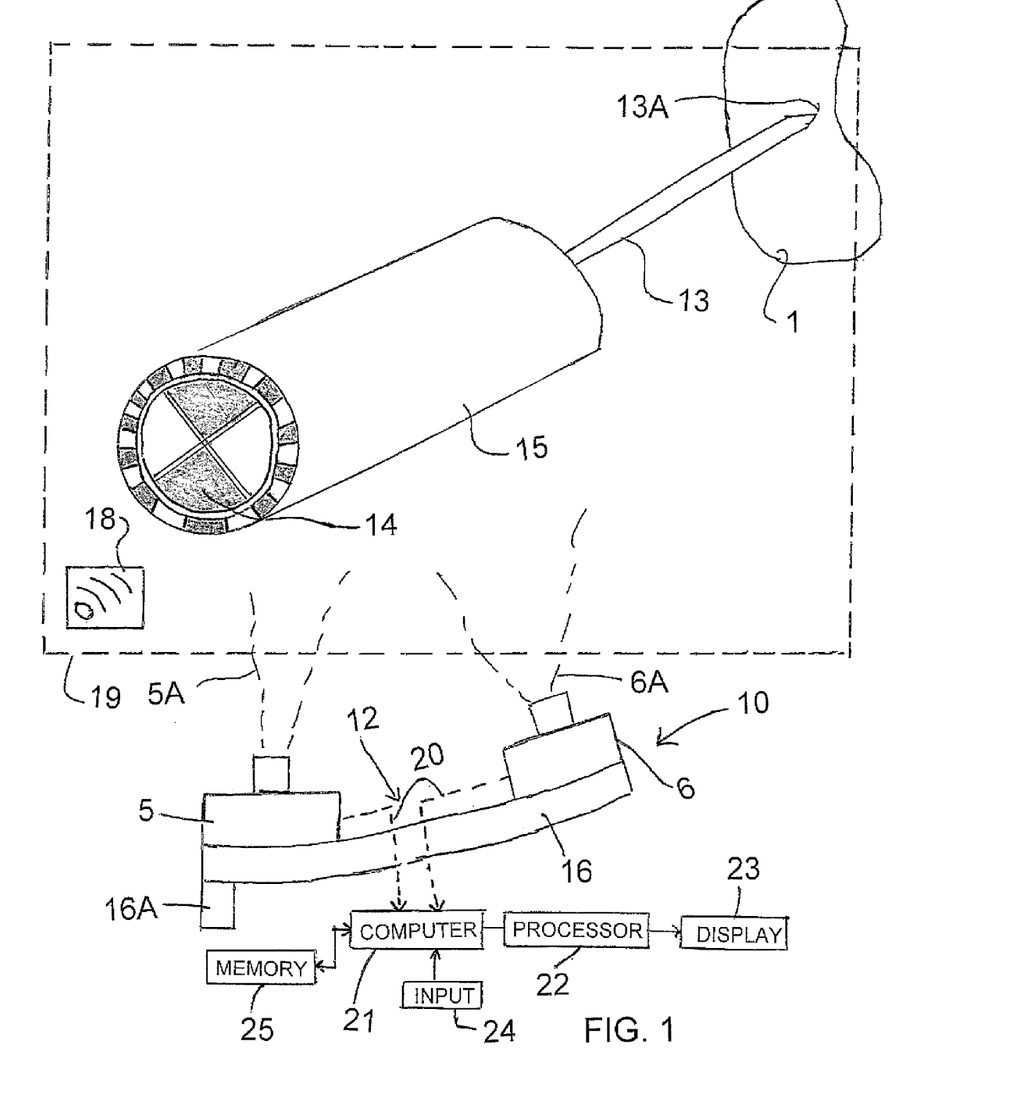
FIG. 1 is a schematic illustration of a system according to the present invention for detecting the location and orientation of an object such as the surgical tool as illustrated.

Referring to FIG. 1, a tracking system 10 has an optical sensor assembly 12 used to track the relative position and orientation of a marker 14 attached to an object 15, such as but not limited to a surgical tool 13 tracked in relation to a portion of a patient's anatomy 1 in a surgical scene or field of view 19. The sensor assembly 12 is a stereo sensor having a first digital video camera sensor with a first field of view 5A and a second digital video camera sensor 6 with a second partially overlapping field of view 6A. More than two cameras 5, 6 could also be used if desired. Suitable sensors or detector arrays for this purpose are commercially available. Such cameras are typically delivered pre-calibrated to allow the association of a pixel position in each of the images with a corresponding linear ray equation in a common sensor 3D space.

The position and orientation of the cameras 5, 6 with respect to one another are fixed by rigidly securing the cameras to a support frame 16, so as to provide for the overlapping views 5A, 6A. The support frame 16 is securely mounted to a fixed support 16A, with an adjustable joint to provide adjustment capability to the direction and proximity of the field of views 5A, 6A to the field of view 19 containing the patient anatomy 1 and the tool 13. The cameras 5, 6 have multiple lines of sight vectors which are contained within their respective fields of view 5A, 6A. A source of illumination 18 can include light energy to supplement visible light already present at the scene, such as existing room lighting or sunlight.

The marker 14, as described in more detail hereinafter, is securely coupled to the tool 3, such that the projection images of marker 14 can be sensed by the cameras 5, 6 when positioned in the corresponding fields of view 5A, 6A. The cameras 5, 6 record projections of all items in the scene 19. These image projections are oriented typically perpendicular to the lines of sight 31, 33. For example, a projected image representing the marker is recorded by the cameras 5 and 6 respectively. A series of image intensity signals 38 representing the projected images of the marker 14 are transmitted by the cameras 5, 6 to the computer 21, where the signals 20 are processed to calculate the three dimensional location of the center of each marker 14. These signals 20 contain image pixel information of the projected images for all the objects 15 and markers 14 present in the scene 19. It is noted that the projected images are typically located as formed on a sensor plane (not shown) inside the camera sensors 5, 6. Accordingly, the position and orientation of the tip 13A of the tool 13, relative to the position of the anatomy 1, is determined by a processor 22 of the computer 21 using the known spatial relationship between the marker 14 and the tip 13A, as the tool 13 is moved about the anatomy 1 in the surgical scene 19 during an operation, or about an anatomical model (not shown) for a simulated planning procedure. The position and orientation information is calculated using the image intensity values of the pixels contained in the signals 20. In this manner, the orientation of the specially marked tool 13 is tracked when moving unpredictably through the field of view 19. The orientation of the anatomy 1 and the tool 13 can be determined relative to a fixed reference point, such as the fixed support 16A.

The processor 22 is coupled to a display 23 and to user input devices 24, such as a keyboard, mouse, or other suitable devices. A computer readable storage medium 25 is coupled to the processor 22 for providing instructions to the processor 22 to perform steps or algorithms related to the determination of the relative spatial position of the tool 13 with respect to the anatomy 1, as well as monitoring the presentation of the anatomy 1 and tool 13 images on the display 23.

Figures 2, 3:
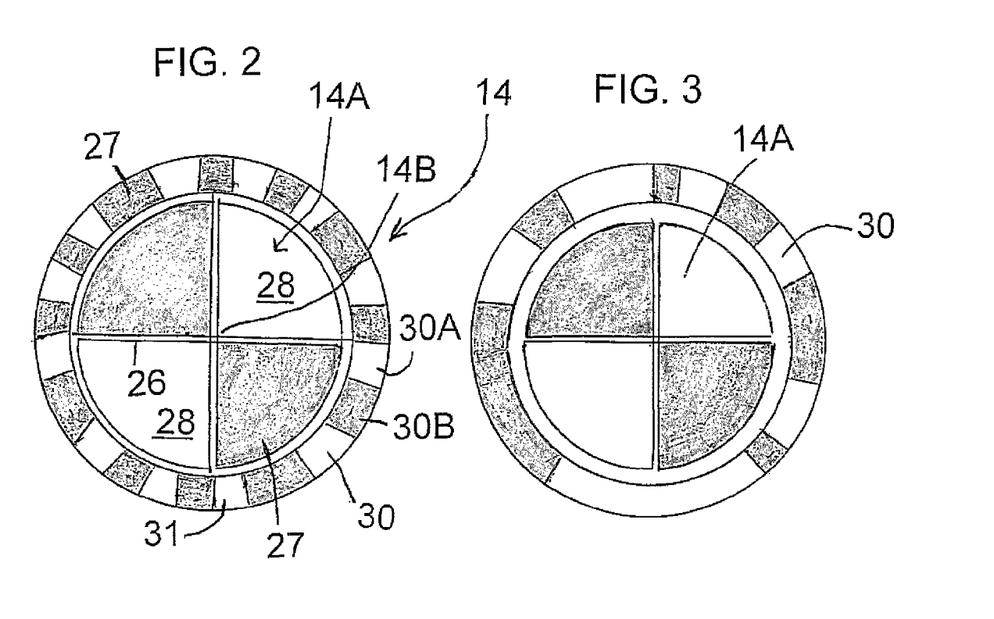
FIGS. 2, 3 and 4 show a front face of three embodiments of marker as used in the system of FIG. 1.
Figure 4:
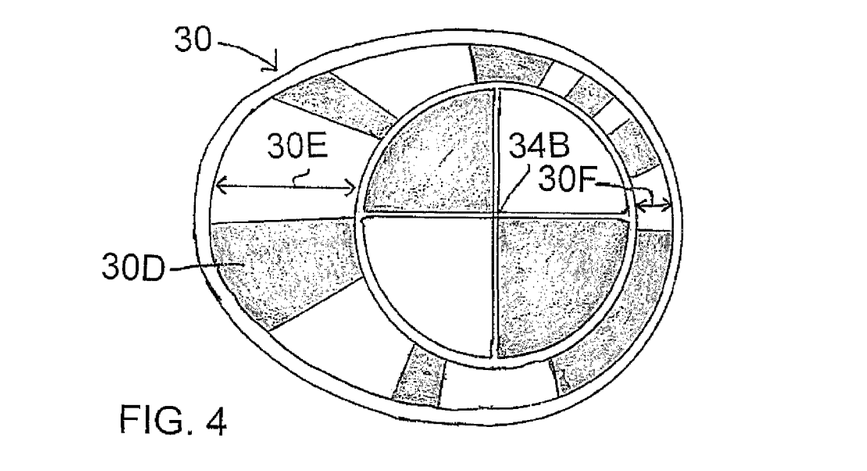

As shown in FIGS. 2, 3 and 4, further details of the markers 14 are provided. Each of the object markers 14 is made up of a target pattern 14A which is a visible high-contrast pattern appearing on a surface of the marker 14. Each visible target pattern 14A has one feature point 14B which is an arrangement of light reflectance in the target pattern 14A which is arranged such that the target pattern 14A and the feature point 14B will be easy to detect using an orientation detection algorithm performed by the computer system 21 and the processor 22 under a wide range of rotation angles, sizes and lighting conditions of the marker 14.

The feature point 14B is defined as an intersection of straight edges 26 formed between alternating dark 27 and bright 28 regions. Such intersections do not commonly occur naturally in images and preferably maintain their pattern characteristics of being an intersection of straight edges 26 under all viewing angles, magnifications, blurring, and perspective distortion that can be encountered by the camera sensors 5, 6 in viewing the marker 14 in the scene 19.

These feature points 14B are also detectable from a wide range of possible appearances in the image using an orientation detection algorithm. For example, stepping along a circle surrounding the feature point 14B will yield a fixed number of alternating intensity peaks and valleys and the direction of the intensity gradients at the strongest edges between each such peak and valley pair is substantially tangential to the circle. The peaks and valleys of the intensity gradients result from the alternation of dark 27 and light 28 contrast regions located within the circle.

The pattern thus includes first components 26 and 27 arranged such that the processor is able to detect a specific location on the marker, that is, the feature point 14B which defines a center of the marker. In the present arrangement, the marker can operate with only a single feature point 14B.

The pattern further includes second components 30 which are arranged to be unique to the marker 14 concerned and thus are different from other markers of the system. These second components are arranged such that the processor is able to distinguish the marker concerned from the other markers. As shown in FIGS. 2, 3 and 4, the second components are arranged in an array 31 extending partly or wholly around the feature point 14B. In the embodiments shown, the array 31 extends fully around the feature point 14B as a complete ring centered on the feature point 14B. The second components 30 define a series of bars of light and dark 30A and 30B of different width centered around the location or feature point 14B. These thus form different sized curved line segments centered around the location which allows an encoding based on the length and number of the line segments, such as a typical 2D bar code.

The fact that the components to be scanned and analyzed are arranged in an array or ring centered on the feature point 14B allows the analysis system defined by the processor to locate the feature point 14B as a first step and then to look for the components around the center defined by the found feature point 14B.

Figure 6:
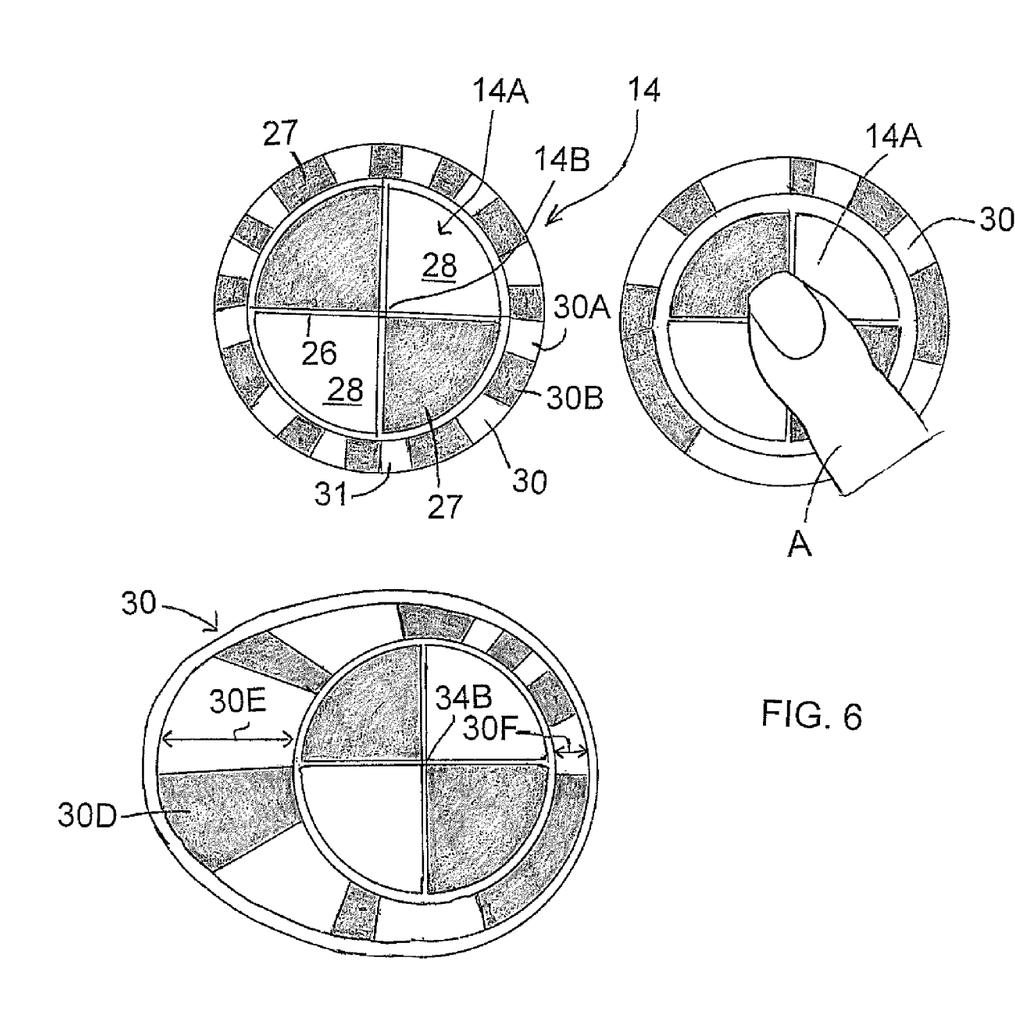
FIG. 6 show a front face of a series of markers used for inputting information by the user selecting one of the markers and pointing to it to occlude part of its pattern.

As shown in FIG. 6, the pattern 30 also can include components of the array arranged around the feature point 14B arranged to define a base line 30D such that the processor is able to detect an angle of rotation of the pattern around the location. Thus the analysis system can locate on the pattern 30 the base line 30D and can measure the angle of rotation of this base line relative to a nominal axis in the detection array In FIG. 6, the pattern 30 is offset to one side of the location so as to define a larger dimension 30E on the side defining an axis for determining the rotation around the location as opposed to the opposite side 30F. Thus the system looks for the array around the point 14B and analyzes it for the encoded data defining the unique marker and then also for the location and orientation of the base line 30D In this way, the marker is arranged such that the detector array and the processor can identify and measure the translational and rotational position of the marker.

As shown in FIG. 3, there is shown an alternative encoding system which uses colour information in the pattern 14A and/or in the pattern 30 to uniquely identify the marker and/or to detect the angular position of the marker.

The camera technology used in the cameras 5 and 6 can be monochromatic, full colour or can use only one of the colour channels.

The object can be a surgical tool as shown. The object can also be non-surgical equipment such as booms, MRI, C-Arms and lights. The object can also be a component of a surgical robotic system, where knowing the precise location of the end effector is critical and where end effector real estate is limited.

The markers are preferably flat disks' as shown with the patters located in a common flat plane of the marker face. However the markers can also have a curved or spherical face.

Figure 5:
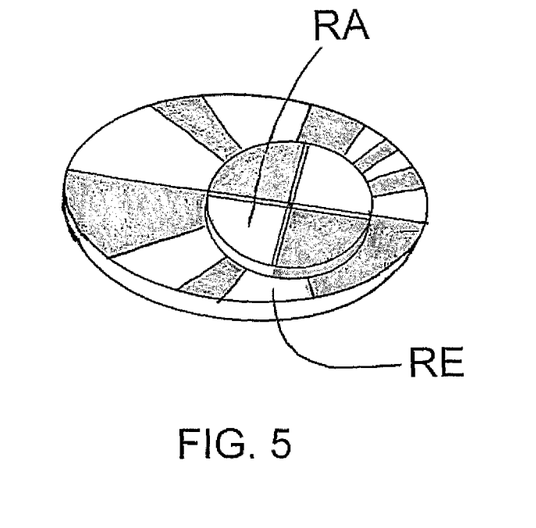
FIG. 5 shows a front face of a further embodiment of marker as used in the system of FIG. 1.

FIG. 5 shows a front face of a further embodiments of marker as used in the system of FIG. 1 where a part of the front face of the marker is raised or recessed so that three dimensional information can be used by detecting the raised and/or recessed sections to uniquely identify the marker and/or to detect the angular position of the marker. Thus the three dimensional information is provided by raised areas RA and/or depressed areas RE of relief on the marker.

In FIG. 6 there is provided a series of markers 14 which can be selected by a user touching or pointing to a selected one of the markers. The processor is arranged to use information identifying each of a series of the markers as an input for process control. This can be used for a virtual keyboard or for gesture control.

Thus the processor is arranged to detect which marker is being selected by determining an area A of occlusion of the marker in the image, such as for example by the location of the user's finger over the marker so that the camera system can no longer see the whole of the marker in the image. It will be appreciated that the arrangement and identification of the markers is carried out by the system prior to the selection by the user. On prompting by the system or as required, the user then occludes a part of one of the markers as shown which is detected by the processor and used as an input such as a switch or a keystroke in accordance with the programming of the system.

Also, the occlusion of the marker 28 can be used to input a graded or variable input, such as a volume control, by the user acting to move the area of occlusion on the marker. For example the user may rotate the finger around the center of the marker to input a degree of increase or decrease of a value indicated by the marker. The processor is arranged to detect the movement and to use the movement as an input for process control.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A surgical robotic system comprising:
a plurality of elements for use in the surgical robotic system at least some of which are movable;
and an imaging system for tracking movement of the movable elements comprising:
a plurality of markers;
each of the movable elements having physically attached thereto at least one of the markers with the marker being attached to the movable element so that it is moved with the movable element;
a camera system for detecting visible light including at least one camera with a detector array for detecting light in a field of view and providing an output responsive thereto;
a processor arranged to analyze the output;
wherein each of the markers includes a pattern thereon which is detectable by the detector array to be analyzed by the processor;
wherein the pattern on each of the markers includes a first component including at least four adjacent areas which surround a central point and intersect at the central point, where each area is of contrasting appearance from each of its neighbouring areas such that the processor is able to detect a specific location point defined by said central point;
wherein the pattern on each of the markers defines only a single central point thereon;
wherein the pattern on each of the markers includes a second component formed by a series of spaced bars of contrasting appearance from a space between the bars;
the bars providing an encoding readable by the processor with the encoding of each marker being different from the other markers to enable the processor to distinguish each marker from the other markers;
and wherein the bars are arranged in a ring surrounding the first component and the central point and are angularly spaced around the ring.

2. The system according to claim 1 wherein the ring forms an ellipse with a major axis so that the processor is able to detect using the major axis an angle of rotation of the pattern around the central point.

3. The system according to claim 1 wherein the marker is arranged such that the detector array and the processor can identify and measure the translational and rotational position of the marker.

4. The system according to claim 1 wherein the second components include the use of colour information provided by areas of different color on the marker.

5. The system according to claim 1 wherein the second components include the use of three dimensional information provided by raised and/or depressed areas of relief on the marker.

6. The system according to claim 1 wherein the marker is passive.

7. The system according to claim 1 wherein the marker includes active illumination.

8. The system according to claim 1 wherein the elements comprise one or more of a CT machine, PET machine, X-Ray machine, OR Table, Ultrasound equipment, stationary wand, hand-held objects, booms, MRI machine, C-Arms and lights.

9. The system according to claim 1 wherein the processor is arranged to detect an area of occlusion of each of a plurality of the markers in the image and to use the detection of the area of occlusion as an input for process control.

10. The system according to claim 9 wherein the processor is arranged to is arranged to identify each of a series of the markers having an area of occlusion and to use the information identifying the markers as an input for process control.

11. The system according to claim 10 wherein the processor is arranged to detect the movement of the occlusion relative to the marker and to use the movement as an input for process control.

12. A surgical robotic system comprising:
a plurality of elements for use in the surgical robotic system at least some of which are movable;
and an imaging system for tracking movement of the movable elements comprising:

a plurality of markers;

each of the movable elements having physically attached thereto at least one of the markers with the marker being attached to the movable element so that it is moved with the movable element;

a camera system for detecting visible light including at least one camera with a detector array for detecting light in a field of view and providing an output responsive thereto;

a processor arranged to analyze the output;

wherein each of the marker includes a pattern thereon which is detectable by the detector array to be analyzed by the processor; and wherein the pattern on each of the markers includes components different from other markers of the system arranged to provide an encoding such that the processor is able to distinguish each marker from the other markers;

wherein the processor is arranged to detect an area of occlusion of each of a plurality of the markers in the image and to use the detection of the area of occlusion as an input for process control.

13. The system according to claim 12 wherein the processor is arranged to detect the movement of the occlusion relative to the marker and to use the movement as an input for process control.

14. The system according to claim 12 wherein the processor is arranged to identify each of a series of the markers having an area of occlusion and to use the information identifying the markers as an input for process control.

15. The system according to claim 1 wherein the ring is circular.

16. The system according to claim 1 wherein the ring is elliptical.

* * * * *